(12) United States Patent  
Yoshida et al.

(10) Patent No.: US 8,021,047 B2  
(45) Date of Patent: Sep. 20, 2011

(54) IMAGE CAPTURING CONTROL APPARATUS

(75) Inventors: Yutaka Yoshida, Kanagawa (JP); Keiji Tsubota, Kanagawa (JP); Takeshi Kamiya, Kanagawa (JP); Yasunori Ohta, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 99 days.

(21) Appl. No.: 12/561,278

(22) Filed: Sep. 17, 2009

(65) Prior Publication Data

US 2010/0080437 A1    Apr. 1, 2010

(30) Foreign Application Priority Data

Sep. 29, 2008   (JP) ................................. 2008-251031

(51) Int. Cl.  
*G01D 18/00* (2006.01)

(52) U.S. Cl. ....................................... 378/207; 378/114

(58) Field of Classification Search ............... 378/98, 378/114, 117, 207  
See application file for complete search history.

(56) References Cited

U.S. PATENT DOCUMENTS

| 7,476,027 B2* | 1/2009 | Takenaka et al. ............. 378/116 |
| 2004/0101093 A1* | 5/2004 | Matsumoto ..................... 378/22 |
| 2006/0285637 A1* | 12/2006 | Varjonen et al. ................ 378/62 |

FOREIGN PATENT DOCUMENTS

| JP | 08155045 A * | 6/1996 |
| JP | 2001-037749 A | 2/2001 |
| JP | 2003-210450 A | 7/2003 |

* cited by examiner

*Primary Examiner* — Glen Kao  
(74) *Attorney, Agent, or Firm* — Solaris Intellectual Property Group, PLLC

(57) ABSTRACT

There is provided an image capturing control apparatus including: a communication unit which communicates with a radiographic imaging apparatus which captures a radiographic image represented by irradiated radiation and generates image information indicating the captured radiographic image; a radiation irradiating unit which is provided with a radiation source for generating the radiation and irradiates the radiation from the radiation source; a storage unit which stores correction information for correcting the radiographic image generated by the radiographic imaging apparatus; and a controller which controls an alarm unit to issue an alarm in a case where the radiation source provided to the radiation irradiating unit or a part which influences irradiation by the radiation source is replaced.

6 Claims, 7 Drawing Sheets

IMAGE CAPTURING CONTROL APPARATUS

CROSS-REFERENCE TO RELATED APPLICATION

This application is based on and claims priority under 35 USC 119 from Japanese Patent Application No. 2008-251031 filed on Sep. 29, 2008, the disclosure of which is incorporated by reference herein.

BACKGROUND

1. Technical Field

The present invention relates to an image capturing control apparatus.

2. Related Art

Recently, a flat panel detector (FPD) that is constructed by disposing a radiation sensitive layer on a thin film transistor (TFT) active matrix substrate has been put to practical applications. The FPD can directly convert a radiation into a digital data. A portable radiographic imaging apparatus (hereinafter, referred to as an "electronic cassette") for generating image information indicating a radiographic image represented by a radiation irradiated by using the FPD and storing the generated image information has been put to practical applications.

Since the electronic cassette has a portability, a patient loaded on a stretcher or a bed can be image captured. In addition, since an imaging portion can be adjusted by changing a position of the electronic cassette, even an immobile patient can be adaptively imaged.

In the electronic cassette, the embedded FPD or an amplifier circuit has unique characteristics. In addition, the electronic cassette can be carried with a hand, and the electronic cassette can be connected to other control apparatuses (so called a "console"). Therefore, one electronic cassette can be circulatively used in other imaging rooms.

Therefore, in the console, data of correction such as shading correction need to be stored for every electronic cassette.

Japanese Patent Application Laid-Open (JP-A) No. 2001-37749 discloses a technique of performing a process of correcting a captured image. Each of electronic cassettes is designated with ID information, and correction tables corresponding to the ID information are stored in a console. A correction table corresponding to the ID information of a specific electronic cassette connected to the console is searched, and the captured image is corrected based on the correction table obtained by the searching of the correction table.

In addition, JP-A No. 2003-210450 discloses a technique where correction information of replacement parts such as an FPD is preliminarily recorded, and when a part is replaced, the preliminarily recorded correction information is transmitted to a flash memory of the replaced part.

However, the shading correction is determined according to a combination of a radiation source and the electronic cassette as well as the electronic cassette. Therefore, in a case where the radiation source of the imaging apparatus is replaced, if the previous correction data for the replacement is still used, an image quality of a radiographic image obtained from the electronic cassette is lowered.

SUMMARY

The present invention is to provide an image capturing control apparatus capable of suppressing an image quality of a radiographic image obtained by a radiographic imaging apparatus from being lowered.

According to an aspect of the invention, there is provided an image capturing control apparatus including:

a communication unit which communicates with a radiographic imaging apparatus which captures a radiographic image represented by irradiated radiation and generates image information indicating the captured radiographic image;

a radiation irradiating unit which is provided with a radiation source for generating the radiation and irradiates the radiation from the radiation source;

a storage unit which stores correction information for correcting the radiographic image generated by the radiographic imaging apparatus; and a controller which controls an alarm unit to issue an alarm in a case where the radiation source provided to the radiation irradiating unit or a part which influences irradiation by the radiation source is replaced.

According to the invention, a radiographic imaging apparatus which captures a radiographic image represented by an irradiated radiation and generates image information indicating the captured radiographic image communicates with a communication unit, and a radiation irradiating unit provided with a radiation source for generating the radiation irradiates the radiation from the radiation source.

In addition, according to the invention, a storage unit stores correction information for correcting the radiographic image generated by the radiographic imaging apparatus.

In addition, according to the invention, a controller controls an alarm unit to issue an alarm in a case where the radiation source provided to the radiation irradiating unit or a part which influences irradiation of the radiation source is replaced.

In this manner, according to the invention, by generating correction information when an alarm is issued, it is possible to suppress an image quality of a radiographic image obtained by the radiographic imaging apparatus.

In addition, each radiographic imaging apparatus may be designated by identification information, and the storage unit may store the correction information for correcting the radiographic image generated by a respective radiographic imaging apparatus for each radiographic imaging apparatus.

Each radiographic imaging apparatus and radiation source may be respectively designated by identification information, the storage unit may store the correction information for correcting a radiographic image for each combination of a radiographic imaging apparatus and a radiation source, the image capturing control apparatus may further comprise an acquisition unit which acquires the identification information of a radiographic imaging apparatus which can communicate with the communication unit and identification information of the radiation source which is provided to the radiation irradiating unit, and the controller may control the alarm unit to issue an alarm in a case where the correction information corresponding to the combination of the radiographic imaging apparatus and the radiation source, which is indicated by the identification information of the radiographic imaging apparatus and the radiation source acquired by the acquisition unit, is not stored in the storage unit.

Further, at least one of the radiographic imaging apparatus or the radiation source may designated by identification information, and the other of the radiographic imaging apparatus or the radiation source stores identification information of the apparatus or device that has been used in combination therewith, wherein the image capturing control apparatus may further comprise an acquisition unit which acquires the identification information from the one of the radiographic imaging apparatus or the radiation source, and wherein the controller may control the alarm unit to issue an alarm in a case where the identification information acquired by the acquisition unit is not stored in the other of the radiographic imaging apparatus or the radiation source.

In addition, the controller may control the radiation irradiating unit and the radiographic imaging apparatus to generate the correction information after the alarm unit issues an alarm.

Further, the part may be one of a cathode, an anode, or a filter.

According to the invention, correction information for correcting the radiographic image generated by the radiographic imaging apparatus is stored in the storage unit, and if the radiation source disposed to the radiation irradiating unit or the part which influences irradiation of the radiation source is replaced, the alarm unit issues an alarm. Accordingly, when the alarm is issued, by generating correction information, deterioration of the image quality of the radiographic image obtained from the radiographic imaging apparatus can be controlled.

BRIEF DESCRIPTION OF THE DRAWINGS

Exemplary embodiments of the present invention will be described in detail based on the following figures, wherein.

DETAILED DESCRIPTION

Hereinafter, exemplary embodiments of the present invention will be described in detail with reference to the accompanying drawings.

Firstly, a configuration of a radiation information system 10 according to an exemplary embodiment will be described.

Figure 1:
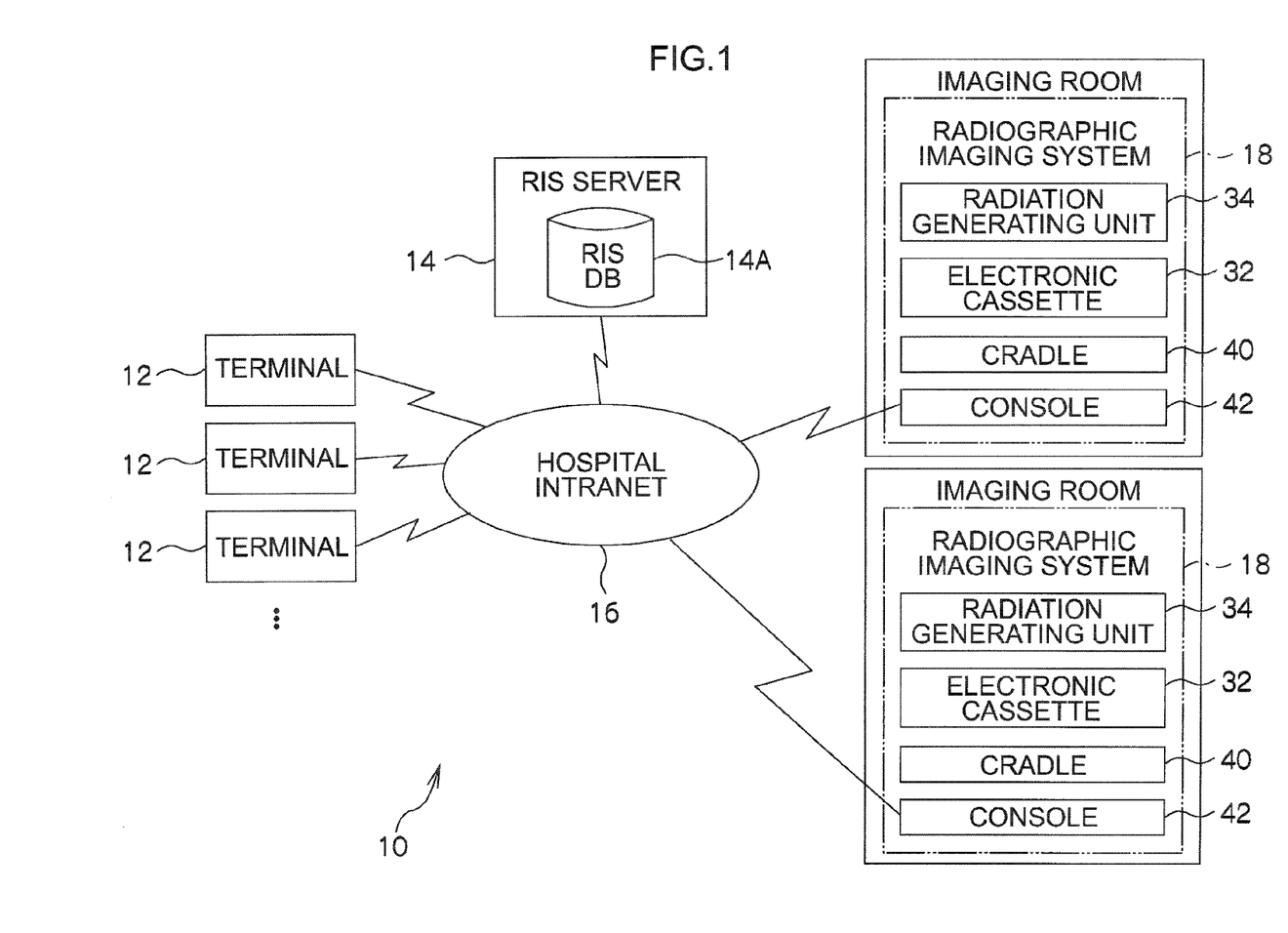
FIG. 1 is a block diagram illustrating a configuration of a radiation information system according to an exemplary embodiment.

FIG. 1 is a block diagram illustrating components of the radiology information system 10 (hereinafter, referred to as an "RIS 10") according to the exemplary embodiment.

The RIS 10 is a system for managing information such as diagnosis reservation and diagnosis record in the department of radiology of a hospital. The RIS 10 constitutes a portion of a hospital information system (HIS).

In the RIS 10, a plurality of imaging-requesting terminals 12 (hereinafter, referred to as a "terminal 12"), an RIS server 14, and a radiographic imaging system 18 installed in each radiographic imaging room (or surgery room) in the hospital are connected to a hospital intranet 16 that is a wired or wireless local are network (LAN). The RIS 10 is constructed as a portion of a hospital information system (HIS) in the same hospital. A HIS server (not shown) which controls a whole of the HIS is connected to the hospital intranet 16.

The terminal 12 is used by a doctor or a radiographic technologist who inputs or searches for the diagnosis information or facility reservation information. The request (that is, reservation) for capturing a radiographic image is also input through the terminal 12. Each of the terminals 12 is constructed with a personal computer attached with a display apparatus. The terminals 12 are connected to the hospital intranet 16 through the RIS server 14, so that the terminals 12 can communicate with each other.

The RIS server 14 receives the request for imaging from the terminals 12. The RIS server 14 manages a schedule of capturing the radiographic image in the imaging system 18. The RIS server 14 includes a database 14A.

The database 14A includes attribute information (name, gender, date of birth, age, blood type, and patient ID, and the like) of a patient, other information (a disease history, a medical examination history, previously-captured images, and the like) of the patient, information (a serial number, a type, a dimension, a sensitivity, an available to-be-imaged portion (details of available imaging request), a use starting data, use times, and the like) of the electronic cassette 32 of the imaging system 18, and an environment for capturing the radiographic image by using the electronic cassette 32, that is, the environment for using the electronic cassette 32 (for example, a surgery room or an imaging room dedicated to capturing the radiographic image).

The imaging system 18 performs capturing of a radiographic image in response to a command from the RIS server 14 according to manipulation of a doctor or a radiographic technologist. The imaging system 18 includes a radiation generating unit 34 that irradiates a radiation X (which becomes an amount of radiation source) from a radiation source (refer to FIGS. 2 and 3) on an imaged object according to an exposure condition, an electronic cassette 32 having a radiation detector 60 (refer to FIG. 3) that detects the radiation X penetrating a patient and converts the detected radiation into radiographic image information, a cradle 40 that charges a battery embedded in the electronic cassette 32, and a console 42 that controls the electronic cassette 32, the radiation generating unit 34, and the cradle 40.

Figure 2:
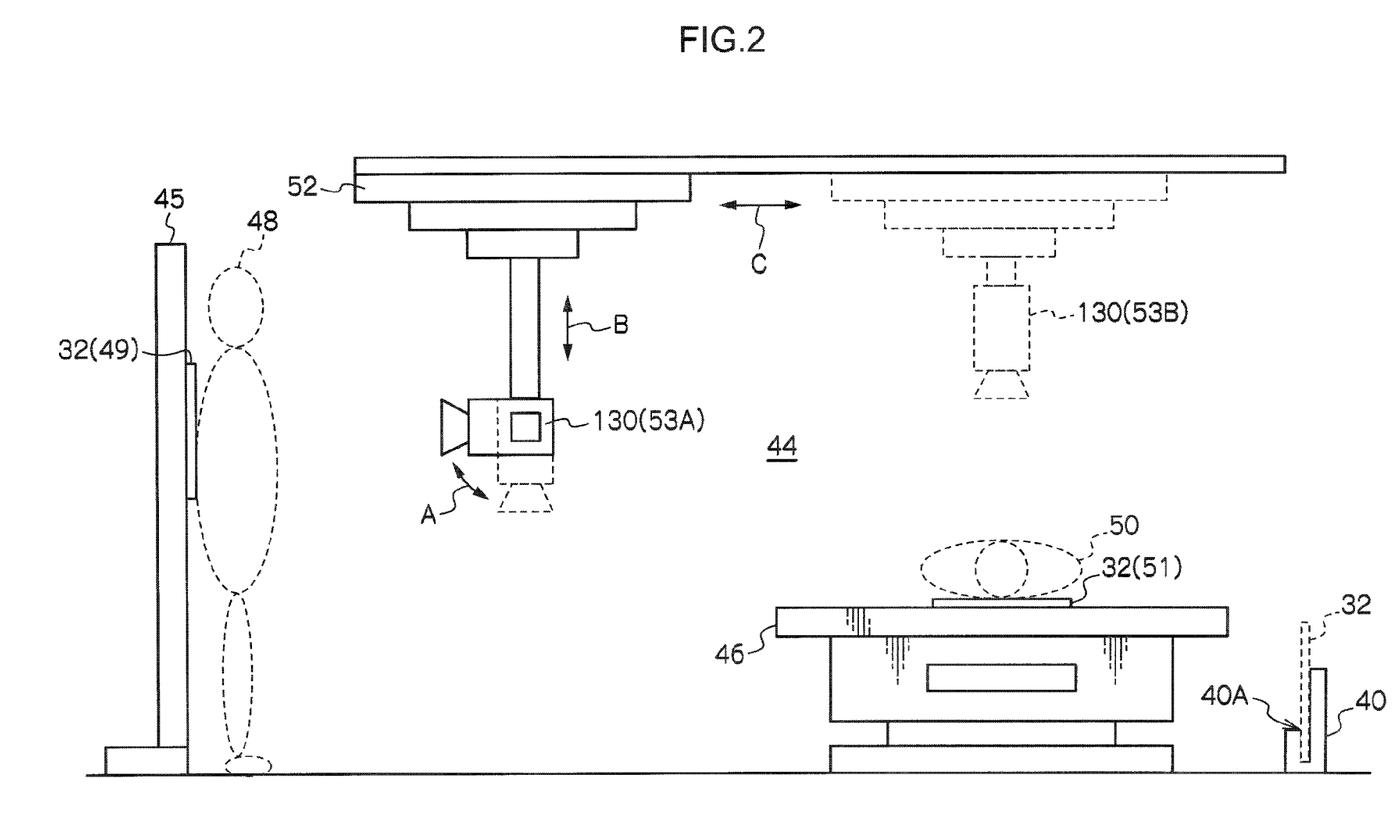
FIG. 2 is a view illustrating a layout of a radiographic imaging room where a radiographic imaging system according to an exemplary embodiment is installed.

FIG. 2 illustrates an example of a layout of a radiographic imaging room 44 where the imaging system 18 according to the invention is installed.

As shown in FIG. 2, in the radiographic imaging room 44, a rack 45 which supports the electronic cassette 32 at the time of radiographic imaging in an erect position and a bed 46 on which a patient lies at the time of radiographic imaging in a lying position are disposed. The front space of the rack 45 is an imaging position 48 of the patient at the time of radiographic imaging in the erect position, and the upper space of the bed 46 is an imaging position 50 of the patient at the time of radiographic imaging in the lying position.

In the radiographic imaging room 44, in order to perform the radiographic imaging in the erect position as well as in the lying position with the radiation from a single radiation source 130, disposed is a movement supporting mechanism 52 which supports the radiation source 130 to be rotated about a horizontal axis (direction of arrow A in FIG. 2), to be moved in the vertical direction (direction of arrow B in FIG. 2), and to be moved in the horizontal direction (direction of arrow C in FIG. 2). The movement supporting mechanism 52 includes a driving source (not shown) for rotating the radiation source 130 about the horizontal axis, a driving source (not shown) for moving the radiation source 130 in the vertical direction, and a driving source (not shown) for moving the radiation source 130 in the horizontal direction.

The cradle 40 is provided with a receiving portion 40A which can receive the electronic cassette 32.

At the standby time, the electronic cassette 32 is received in the receiving portion 40A of the cradle 40 and the battery embedded therein is charged. At the time of radiographic imaging, the radiographic technologist takes the electronic cassette off from the cradle 40. If the imaging posture is in the erect position, the electronic cassette 32 is moved and positioned at the position 49 supported by the rack 45. If the imaging posture is in the lying position, the electronic cassette 32 is moved and positioned at the position 51 on the bed 46.

In the imaging system 18 according to the exemplary embodiment, the radiation generating unit 34 and the console 42 are connected with each other through a cable, so that various kinds of information can be received and transmitted. In FIG. 2, the cables for connecting these components are omitted. In addition, various kinds of information can be received and transmitted through wireless communication between the electronic cassette 32 and the console 42.

In the above description, the electronic cassette 32 is used in the radiographic imaging room 44, but the invention is not limited thereto. For example, the electronic cassette 32 can be used for diagnosis or round visit in a hospital.

Figure 3:
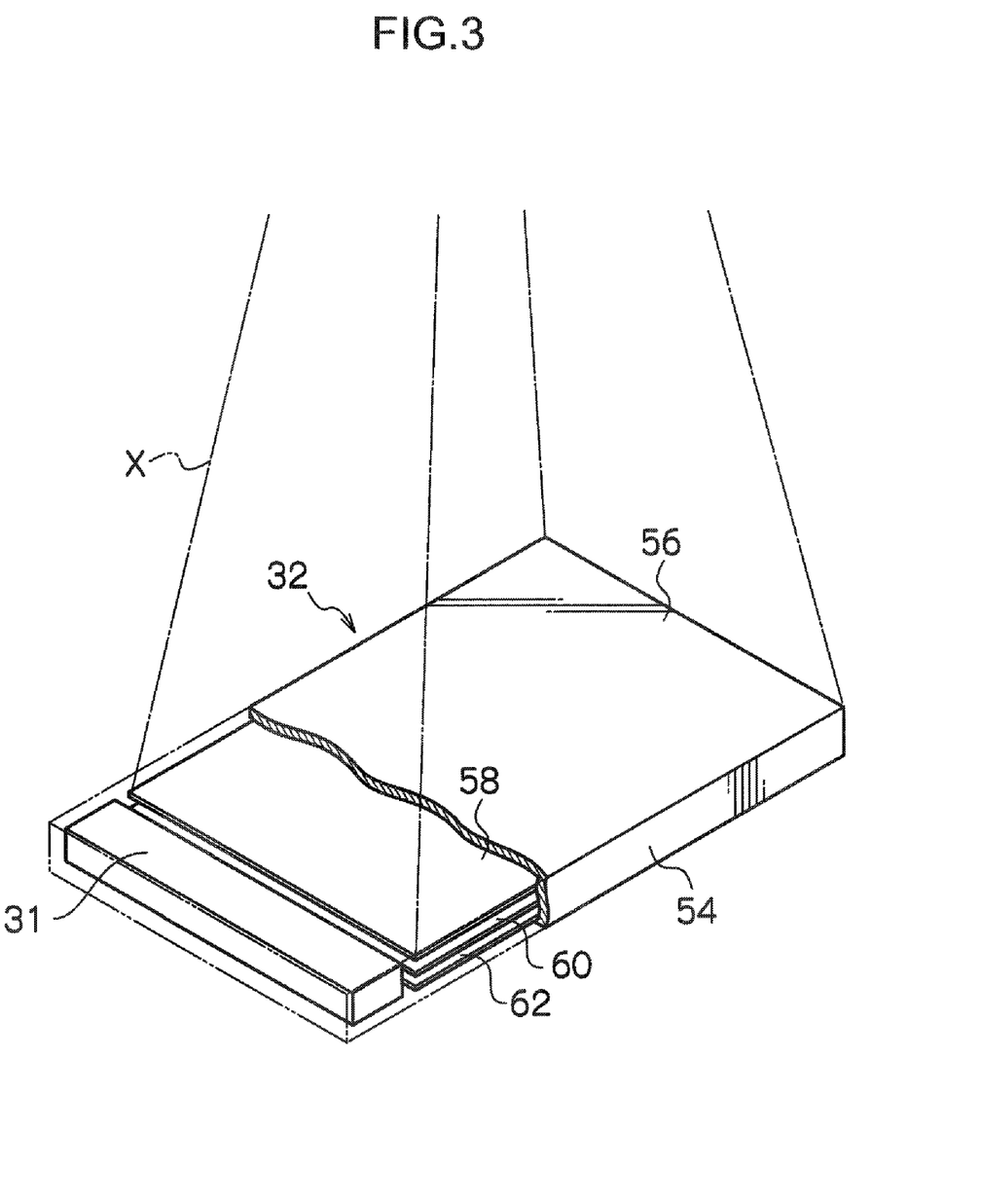
FIG. 3 is a perspective view illustrating an internal construction of an electronic cassette according to an exemplary embodiment.

FIG. 3 illustrates an internal construction of the electronic cassette 32 according to the exemplary embodiment.

As shown in FIG. 3, the electronic cassette 32 has a casing 54 made of a material capable of penetrating a radiation X and has a water-resistant, hermetic structure. When the electronic cassette 32 is used in a surgery room, the electronic cassette 32 may be contaminated by blood or bacteria. Therefore, by sterilizing the electronic cassette 32 having a water-resistant, hermetic structure if needed, one electronic cassette 32 can be repeatedly used.

Within the casing 54, a grid 58 for removing a scattered ray of the radiation X generated from the patient a radiation detector 60 for detecting the radiation X penetrating the patient, and a lead plate 62 for absorbing a back-scattered ray of the radiation X are disposed sequentially from the irradiation surface 56 of the casing 54 irradiated with the radiation X. Alternatively, the irradiation surface 56 of the casing 54 may be constructed with the grid 58.

In addition, a case 31 which receives electronic circuits including a microcomputer and a rechargeable secondary battery is disposed in one end side of the inner portion of the casing 54. The radiation detector 60 and the electronic circuits are operated by power supplied from the secondary battery disposed in the case 31. Preferably, in order to preventing the irradiated radiation X from damaging various circuits received in the case 31, a lead plate is disposed on the irradiation surface 22 of the case 31.

Figure 4:
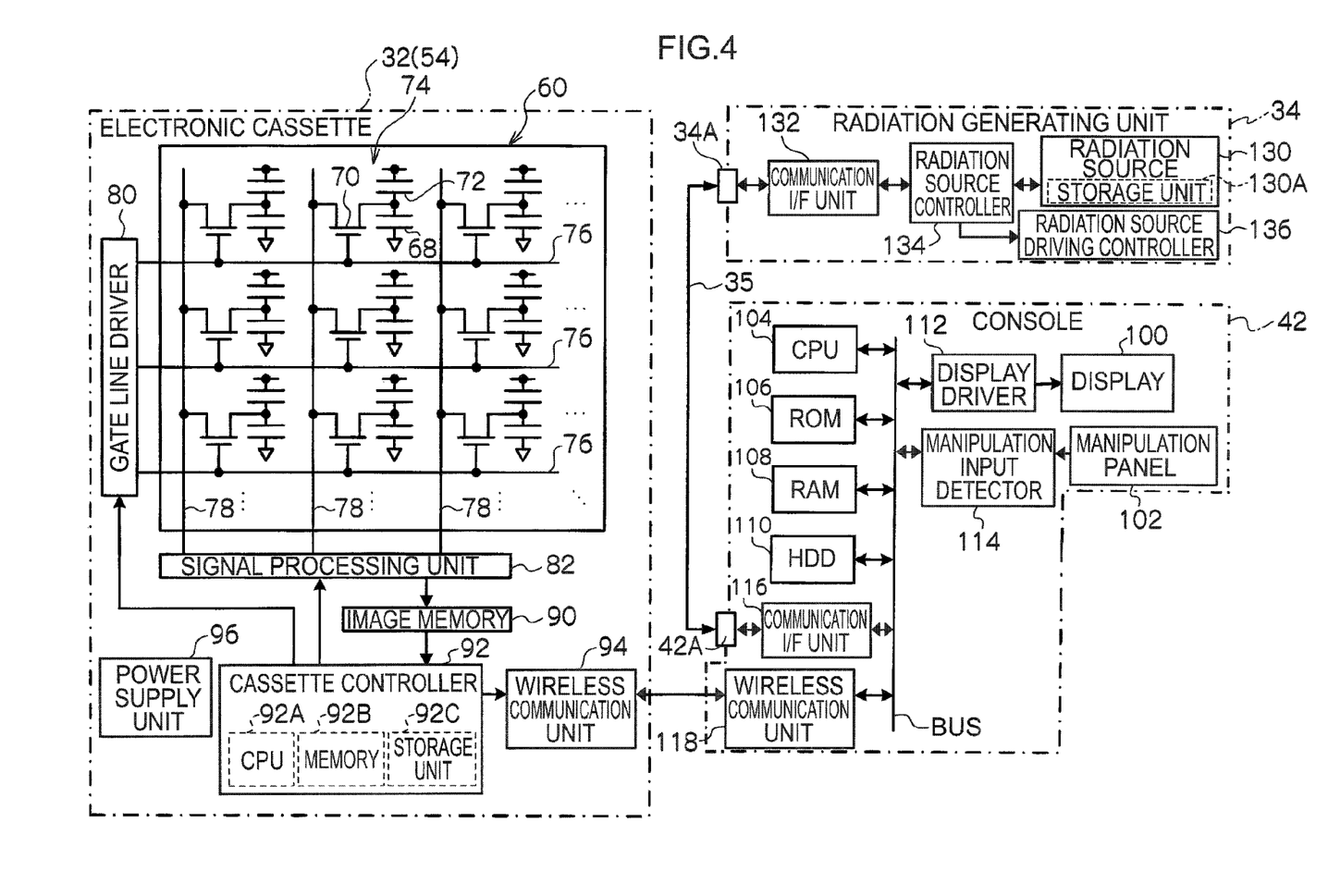
FIG. 4 is a block diagram illustrating a detailed configuration of radiographic imaging system according to an exemplary embodiment.

FIG. 4 is a block diagram illustrating a detailed configuration of the radiographic imaging apparatus 18 according to the exemplary embodiment.

A connection port 34A for communicating with the console 42 is provided to the radiation generating unit 34. A connection port 42A for communicating with the radiation generating unit 34 is provided to the console 42.

The radiation detector 60 embedded in the electronic cassette 32 is constructed by laminating a photoelectric conversion layer of absorbing a radiation X and converting the radiation into charges on the TFT active matrix substrate 66. The photoelectric conversion layer is made of, for example, an amorphous a-Se (amorphous selenium) containing selenium as a main ingredient (for example, a containing ratio of 50% or more). When the radiation X is irradiated, the photoelectric conversion layer converts the irradiated radiation into charges by generating charges (electron-hole pairs) having a charge amount corresponding to the irradiated radiation X amount in an inner portion thereof. The radiation detector 60 is not limited to the aforementioned construction where the radiation is directly converted into the charges by using a radiation-charge conversion material such as the amorphous selenium. Alternatively, the radiation detector 60 may employ a construction where the radiation is indirectly converted into the charges by using a fluorescent material and a photoelectric conversion device (photodiode). As the fluorescent material, gadolinium oxysulfide (GOS) or cesium iodide (CsI) are well known. In this case, radiation-photon conversion is performed by using the fluorescent material, and after that, photoelectric conversion is performed by using the photoelectric conversion device such as a photodiode.

On the TFT active matrix substrate 66, plural pixel units 74 (in FIG. 4, the photoelectric conversion layers corresponding to the pixel units 74 are diagrammatically indicated by photoelectric conversion units 72) including storage capacitances 68 which store the charges generated in the photoelectric conversion layers and TFTs 70 which are used for reading out the charges stored in the storage capacitances 68 are disposed in a matrix. The charges that are generated in the photoelectric conversion layers due to the irradiation of the radiation X on the electronic cassette 32 are stored in the storage capacitances 68 of the pixel units 74. Accordingly, the image information contained in the radiation X irradiated on the electronic cassette 32 is converted into the charge information to be stored in the radiation detector 60.

In addition, in the TFT active matrix substrate 66, disposed are a plurality of gate lines 76 which are disposed to extend in a predetermined direction (row direction) and used for turning on and off the pixel units 74 and plural data lines 78 which are disposed to extend in a direction (column direction) perpendicular to the gate lines 76 and used for reading out the stored charges from the storage capacitances 68 through the turned-on TFTs 70. Each of the gate lines 76 is connected to a gate line driver 80, and each of the data lines 78 is connected to a signal processing unit 82. When the charges are stored in the storage capacitances 68 of the pixel units 74, the TFTs 70 of the pixel units 74 are sequentially turned on in units of row by a signal applied from the gate line driver 80 through the gate lines 76. The charges stored in the storage capacitances 68 of the pixel unit 74 of which TFTs 70 are turned on are transmitted as a charge signal through the data lines 78 to be input to the signal processing unit 82. Accordingly, charges stored in the storage capacitance 68 of each pixel unit 74 are sequentially read out in units of row.

Figure 5:
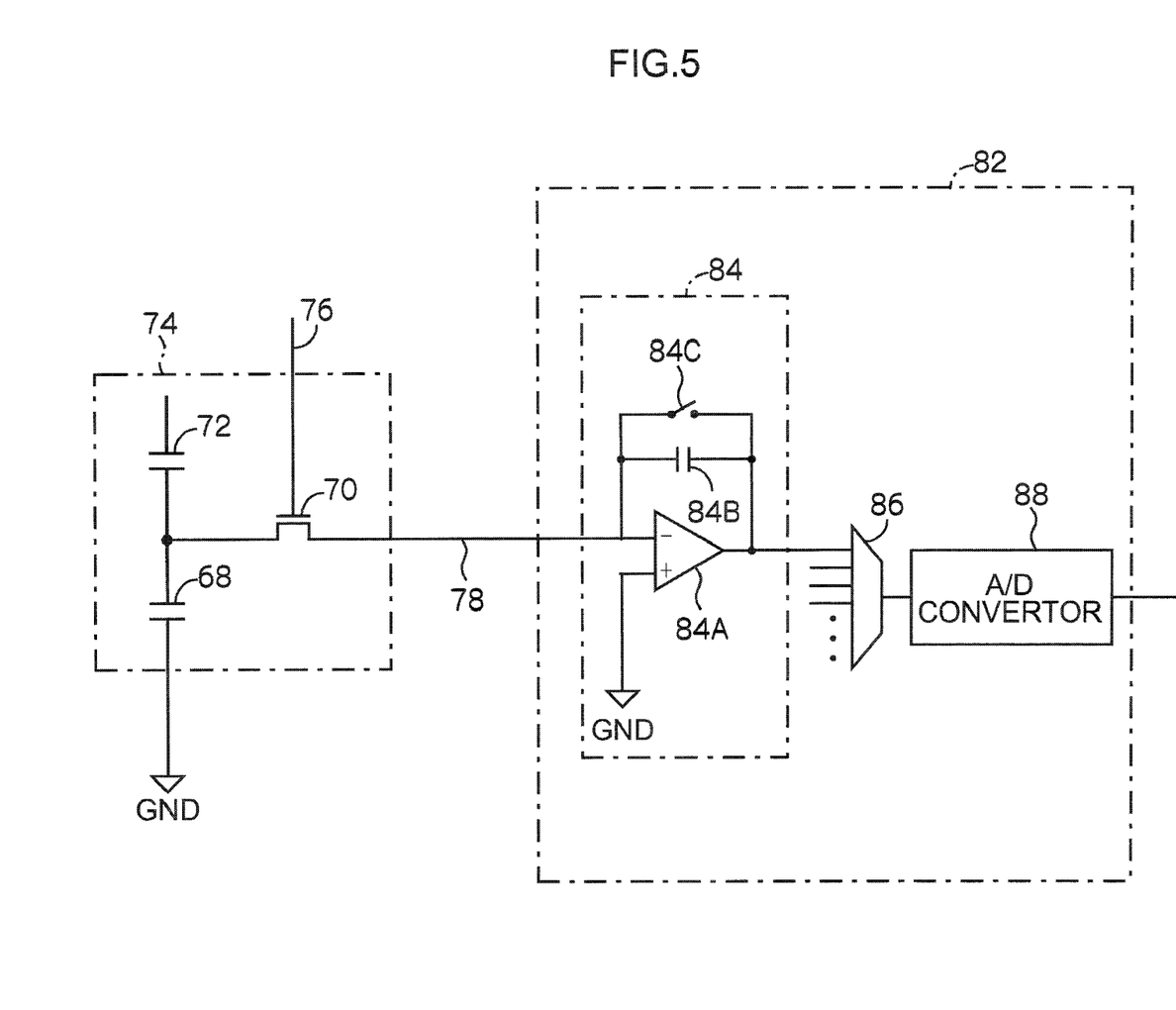
FIG. 5 is an equivalent circuit view illustrating one pixel in a radiation detector according to an exemplary embodiment.

FIG. 5 is an equivalent circuit view illustrating one pixel in the radiation detector 60 according to the exemplary embodiment.

As shown in FIG. 5, the source of the TFT 70 is connected to the data line 78. The data line 78 is connected to a signal processing unit 82. The drain of the TFT 70 is connected to the storage capacitance 68 and the photoelectric conversion unit 72. The gate of the TFT 70 is connected to the gate line 76.

The signal processing unit 82 includes a sample hold circuit 84 for each data line 78. The charge signal transmitted through each data line 78 is stored in the sample hold circuit 84. The sample hold circuit 84 includes an OP Amp 84A and a condenser 84B to convert the charge signal into an analog voltage. In addition, the sample hold circuit 84 is provided with a switch 84C as a reset circuit that allows the two electrodes of the condenser 84B to be short-circuited so as to discharge the charges stored in the condenser 84B.

A multiplexer 86 and an A/D converter 98 are sequentially connected to the output side of the sample hold circuit 84. The charge signal stored in each sample hold circuit is converted into an analog voltage to be sequentially (serially) input to the multiplexer 86. After that, the signal is converted into digital image information by the A/D converter 88.

An image memory 90 is connected to the signal processing unit 82 (refer to FIG. 4). The image information output from the A/D converter 88 of the signal processing unit 82 is sequentially stored in the image memory 90. The image memory 90 has a storage capacity of storing predetermined frames of image information indicating the radiation information. Every time when charges of each line are read out, image information corresponding to one read-out line is sequentially stored in the image memory 90.

The image memory 90 is connected to a cassette controller 92 which controls the entire operations of the electronic cassette 32. The cassette controller 92 includes a CPU 92A implemented with a microcomputer, a memory 92B including an ROM and an RAM, and a non-volatile storage unit 92C such as HDD and a flash memory. Each electronic cassette 32 is designated with identification information for identifying the electronic cassette 32. The identification ID is stored in the storage unit 92C.

The cassette controller 92 is provided with a wireless communication unit 94. The wireless communication unit 94 is in accordance with a wireless local area network (LAN) represented by IEEE (Institute of Electrical and Electronics Engineers) 802.11a/b/g or the like. The wireless communication unit 94 controls wireless communication of various kinds of information with external apparatuses. The cassette controller 92 can wireless communicate with the console 42 through the wireless communication unit 94, so that various kinds of information can be received/transmitted from/to the console 42. The cassette controller 92 stores an imaging condition (described later) that is received from the console 42 and starts reading out charges based on the imaging condition.

In addition, the electronic cassette 32 is provided with a power supply unit 96. The aforementioned various circuits and components (the gate line driver 80, the signal processing unit 82, the image memory 90, the wireless communication unit 94, a microcomputer serving as the cassette controller 92, and the like) are driven by a power supplied from the power supply unit 96. The power supply unit 96 is embedded with a battery (rechargeable secondary battery) in order not to interfere with the portability of the electronic cassette 32. The various circuits and components are supplied with a power by the charged battery.

The console 42 is constructed with a server computer. The console 42 includes a display 100 which displays a manipulation menu, a radiographic image, or the like and a manipulating panel 102 having a plurality of keys, through which various kinds of information or manipulation commands are input.

In addition, the console 42 according to the exemplary embodiment includes a CPU 104 which controls the entire operations of the apparatus, an ROM 106 which stores various programs including a control program, an RAM 108 which temporarily stores various kinds of data, an HDD 110 which stores various kinds of data, a display driver 112 which controls displaying various kinds of information on a display 100, a manipulation input detector 114 which detects a manipulation state of a manipulating panel 102, a communication interface (I/F) unit 116 which is connected to a connection port 42A to perform receiving/transmitting various kinds of information such as an imaging condition (described later) and state information of the radiation generating unit 34 through the connection port 42A and a communication cable 35 between the communication interface (I/F) unit 116 and the radiation generating unit 34, and a wireless communication unit 118 which performs receiving/transmitting various kinds of information such as image capturing control information and image information through wireless communication between the wireless communication unit 118 and the electronic cassette 32.

The CPU 104, the ROM 106, the RAM 108, the HDD 110, the display driver 112, the manipulation input detector 114, the communication I/F unit 116, and the wireless communication unit 118 are connected to each other via a system bus. The CPU 104 can access the ROM 106, the RAM 108, and the HDD 110. The CPU 104 can control displaying of various kinds of information on the display 100 through display driver 112, receiving/transmitting of various kinds of information from/to the radiation generating unit 34 through the communication I/F unit 116, and receiving/transmitting various kinds of information from/to the electronic cassette 32 through the wireless communication unit 118. In addition, the CPU 104 can check a user's manipulation state of the manipulation panel 102 through the manipulation input detector 114.

The radiation generating unit 34 includes a radiation source 130 which outputs a radiation X, a communication I/F unit 132 which receives/transmits various kinds of information such as imaging conditions and state information of the radiation generating unit 34 from/to the console 42, a radiation source controller 134 which controls the radiation source 130 based on the received imaging conditions, and a radiation source driving controller 136 which controls operations of the movement supporting mechanism 52 by controlling a power to be supplied to driving sources provided to the movement supporting mechanism 52.

The radiation source controller 134 is constructed with a microcomputer to store the received imaging condition. The imaging condition received from the console 42 includes irradiation condition information such as a tube voltage, a tube current, and an irradiation time or posture information indicating whether the imaging posture is in an erect position or a lying position. If the imaging posture indicated by the received imaging condition information is in the erect position, the radiation source controller 134 controls the movement supporting mechanism 52 so that the radiation source 130 is disposed at the erect imaging position 53A (refer to FIG. 2, the position where the patient in the imaging position 48 is irradiated from the side of the patient with the emitted radiation) by the radiation source driving controller 136. If the imaging posture indicated by the received imaging condition information is in the lying position, the radiation source controller 134 controls the movement supporting mechanism 52 so that the radiation source 130 is disposed at the lying imaging position 53B (refer to FIG. 2, the position where the patient in the imaging position 50 is irradiated from the upper position of the patient with the emitted radiation) by the radiation source driving controller 136. Accordingly, the radiation X is irradiated from the radiation source 130 based on an exposure condition included in the imaging condition.

In addition, in the radiation generating unit 34 according to the exemplary embodiment, the radiation source 130 is detachably provided, so that a radiation that is worn-out or in disorder can be replaced with a new radiation source. The radiation source 130 is provided with a non-volatile storage unit 130A such as an ROM and a flash memory. Each radiation source 130 is designated with identification information for identifying the radiation source 130. The identification ID for identifying each radiation source 130 is stored in the storage unit 130A. When the radiation source 130 is installed in the radiation generating unit 34, the storage unit 130A is connected to the radiation source controller 134, so that the identification ID stored in the storage unit 130A can be read out by the radiation source controller 134.

Next, operations of the imaging system 18 according to the exemplary embodiment are described.

The radiation detectors 60 and the radiation sources 130 embedded in the electronic cassette 32 may have a variation in characteristics thereof. Therefore, in the radiographic images obtained from photographing, an image quality such as shading may be varied according to every combination of the electronic cassette 32 and the radiation source 130. The console 42 stores in the HDD 110 the correction information for correcting the radiographic image for every combination of the radiation detector 60 to the radiation source 130.

The radiation generating unit 34 is connected through a communication cable 35 to the console 42. In the state of communication with the console 42, the radiation generating unit 34 transmits the identification ID of the radiation source 130 stored in the storage unit 130A through the communication cable 35 to the console 42.

In the state of communication with the console 42, the electronic cassette 32 transmits the identification ID of the electronic cassette 32 stored in the storage unit 92C through wireless communication to the console 42.

When receiving identification ID from each of the electronic cassette 32 and the radiation generating unit 34, the console 42 performs a combination determining process for determining a communication of the electronic cassette 32 and the radiation source 130 indicated by the identification ID.

Figure 6:
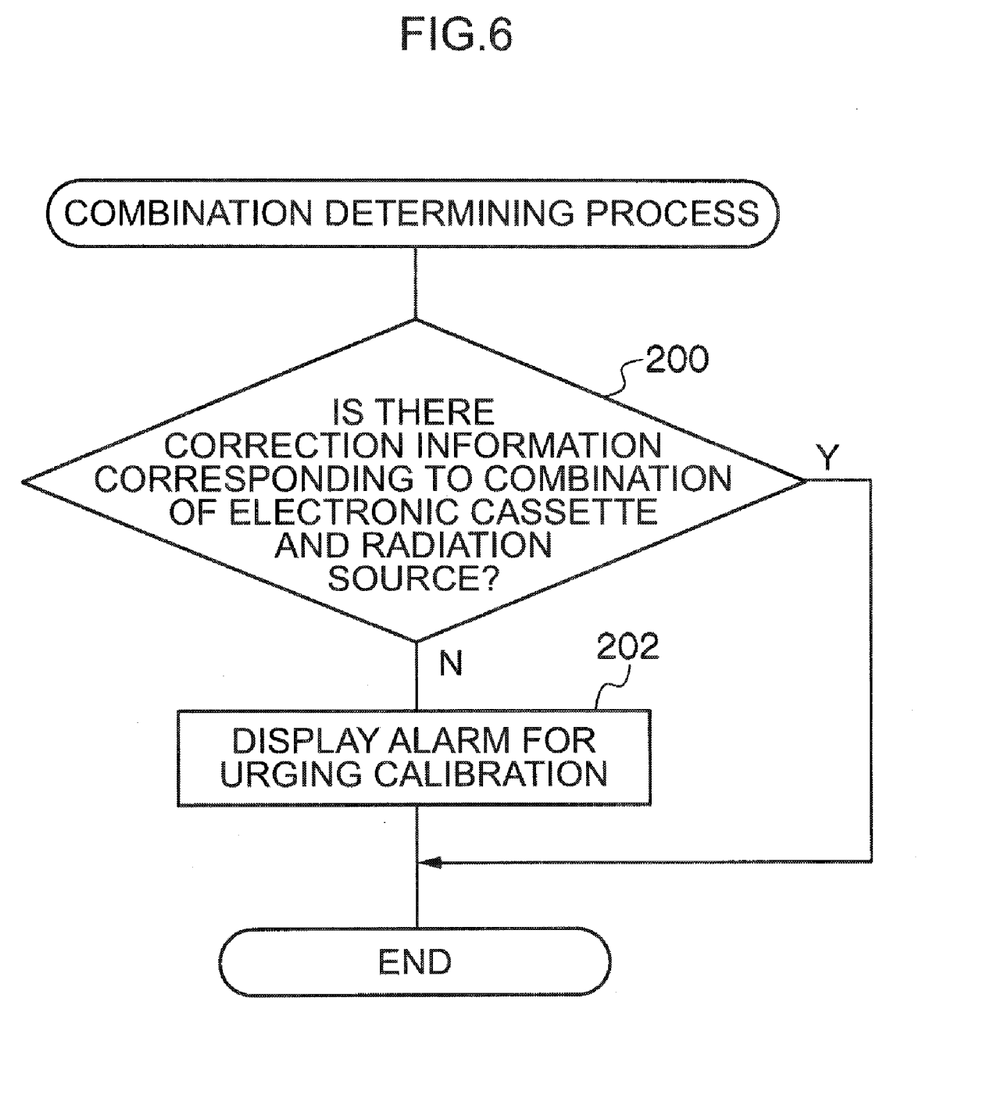
FIG. 6 is a flowchart illustrating a procedure of a combination determining process program according to an exemplary embodiment.

FIG. 6 is a flowchart illustrating a procedure of a combination determining process program executed by the CPU 104. The program is stored in a predetermined region of the ROM 106 or the HDD 110 in advance.

In FIG. 6, in a step 200, it is determined whether or not the correction information corresponding to a combination of the electronic cassette 32 and the radiation source 130 indicated by identification IDs received from the electronic cassette 32 and the radiation generating unit 34 is stored in the HDD 110. If the result of the determination is affirmative, the process is ended. If the result of the determination is negative, the process proceeds to a step 202.

In the step 202, since the combination of the electronic cassette 32 and the radiation source 130 is a new combination, an alarm for urging calibration is displayed on the display 100, and the process is ended.

In the imaging system 18 according to the exemplary embodiment, the calibration is performed by setting a distance (SID) between the electronic cassette 32 and the radiation source 130 in an erect position of the imaging posture to a predetermined imaging distance and irradiating the radiation from the radiation source 130 in a predetermined exposure condition.

If the alarm of urging the calibration is displayed on the display 100, the radiographic technologist mounts the electronic cassette 32 on the rack 45 and performs a predetermined manipulation of commanding the start of calibration on the manipulation panel 102 of the console 42.

If the predetermined manipulation of commanding the start of calibration is performed on the manipulation panel 102, the console 42 transmits to the radiation generating unit 34 and the electronic cassette 32 the imaging condition including the imaging posture set to the erect position, the predetermined imaging distance set to the distance between the electronic cassette 32 mounted on the rack 45 and the radiation source 130, and the exposure condition set to a predetermined exposure condition for calibration. Accordingly, the radiation source controller 134 controls the movement supporting mechanism 52 so that the radiation source 130 is moved to be in the imaging posture for the calibration designated by the received imaging condition.

When the radiation source 130 is in the imaging posture for the calibration, the console 42 transmits the command information indicating the starting of exposure to the radiation generating unit 34 and the electronic cassette 32. Accordingly, the radiation source controller 134 controls the radiation source 130 to irradiate the radiation X based on the exposure condition included in the imaging condition.

The radiation X irradiated from the radiation source 130 is incident on the electronic cassette 32. Accordingly, charges are stored in the storage capacitance 68 of each pixel unit 74 of the radiation detector 60 embedded in the electronic cassette 32.

After elapse of an irradiation time designated by the imaging condition from the time of receiving of the command information indicating the starting of exposure, the cassette controller 92 of the electronic cassette 32 controls the gate line driver 80 to output ON signal to each gate line 76 sequentially in units of one line from the gate driver 80, so that the TFTs 70 connected to the gate lines 76 are turned ON sequentially in units of one line. In the radiation detector 60, when the TFTs 70 connected to the gate lines 76 are sequentially turned ON in units of one line, the charges stored in the storage capacitance 68 are flown as charge signals into the data lines 78 in units of one line. The charges flown into each data line 78 are input to each sample hold circuit 84 to be converted into a voltage signal. The converted voltage signal is sequentially (serially) input to the multiplexer, so that the voltage signal is converted into digital image information by the A/D converter. The image information is stored in the image memory 90. The cassette controller 92 transmits to the image information stored in the image memory 90 through wireless communication to the console 42.

The console 42 generates various kinds of correction information such as shading information based on the received image information and stores in the HDD 100 the correction information corresponding to a combination of the radiation detector 60 and the radiation source 130 indicated by the previously received identification ID.

Next, a procedure of radiographic imaging in the RIS 10 according to the exemplary embodiment is described in brief.

A terminal 12 (refer to FIG. 1) receives a request for imaging including environment information from the doctor or the radiographic technologist. The request for imaging designates an environment where the electronic cassette 32 is used, date of imaging, and imaging condition.

The terminal 12 notifies details of the received request for imaging to the RIS server 14. The RIS server 14 stores the details of the request for imaging notified from the terminal 12 to the database 14A.

The console 42 accesses the RIS server 14 to acquire the details of the request for imaging and the associated environment information from the RIS server 14 and displays the details of the request for imaging on the display 100. In addition, the console 42 transmits the imaging condition of the current radiographic imaging to the radiation generating unit 34 and the electronic cassette 32. Accordingly, the radiation source controller 134 of the radiation generating unit 34 controls the radiation source driving controller 136 so that the radiation source 130 is disposed at the position corresponding to the imaging posture designated by the received imaging condition.

The doctor or the radiographic technologist starts radiographic imaging based on details of the resuest for imaging displayed on the display 100.

As shown in FIG. 2, in a case where radiographic imaging is performed on an affected portion of the patient in the lying position on the bed 46, the doctor or the radiographic technologist disposes the electronic cassette 32 between the bed 46 and the affected portion according to the to-be-imaged portion and angle and disposes the radiation generating unit 34 over the affected portion. In addition, the doctor or the radiographic technologist performs a manipulation of designating an exposure condition such as a tube voltage, a tube current, and an irradiation time, and the like at the time of irradiating the radiation X on the manipulation panel 102 of the console 42 according to the to-be-imaged portion of the patient and the imaging condition. When the imaging condition is changed, the console 42 transmits the imaging condition including a changed exposure condition to the radiation generating unit 34 and the electronic cassette 32.

When the imaging preparation of the radiation generating unit 34 is completed, the doctor or the radiographic technologist performs a manipulation of commanding the imaging on the manipulation panel 102 of the console 42. If the manipulation of commanding the imaging is performed on the manipulation panel 102, the console 42 transmits information of commanding the starting of exposure to the radiation generating unit 34 and the electronic cassette 32. Accordingly, the radiation source 130 generates and emits the radiation having a radiation amount corresponding to the exposure condition included in the imaging condition information which the radiation generating unit 34 receives from the console 42.

The radiation X irradiated from the radiation source 130 penetrates the patient, and after that, the radiation X is incident on the electronic cassette 32. Accordingly, charges are stored in the storage capacitance 68 of each pixel unit 74 of the radiation detector 60 embedded in the electronic cassette 32.

The charges stored in the storage capacitance 68 of each pixel unit 74 in the radiation detector 60 are read out by the gate line driver 80 and the signal processing unit 82 and converted into the image information. The image information is stored in the image memory 90. The image information stored in the image memory 90 is transmitted through wireless communication to the console 42.

The console 42 reads out from the HDD 110 the correction information corresponding to a combination of the radiation detector 60 and radiation source 130 that are used for the imaging. The console 42 performs an image process of correcting the received image information with the correction information and stores the corrected image information to the HDD 110. The image information stored in the HDD 110 is displayed on the display 100 so as to be used for checking the captured radiographic image and, at the same time, transmitted to the RIS server 14 so as to be stored in the RIS database. Accordingly, the captured radiographic image is displayed on the terminal 12, so that the doctor performs reading of the radiographic image and diagnosis.

In this manner, according to the exemplary embodiment, the correction information for correcting the radiographic image for every combination of the electronic cassette 32 and the radiation source 130 is stored in the HDD 110. In a case where the correction information corresponding to the combination of the electronic cassette 32 which used for imaging in a communicatable manner through the wireless communication unit 118 and the radiation source 130 which is provided to the radiation generating unit 34 is not stored in the HDD 110, an alarm is issued. If the alarm is issued, by generating the correction information corresponding to the combination of the electronic cassette 32 and the radiation source 130, deterioration of an image quality of the radiographic image obtained by the electronic cassette 32 can be suppressed.

In the above exemplary embodiment, the invention is adapted to the electronic cassette, that is, a portable radiographic imaging apparatus, but the invention is not limited thereto. For example, the invention may also be adapted to a stationary radiographic imaging apparatus. In addition, the communication between electronic cassette 32 and the console 42 may be wired communication.

In addition, in the above exemplary embodiment, the calibration of the imaging system 18 is performed in the erect imaging posture, but the invention is not limited thereto. For example, the calibration may be performed in the lying imaging posture.

In addition, in the above exemplary embodiment, the electronic cassettes 32 and the radiation sources 130 are designated with identification IDs and the correction information for correcting the radiographic image for every combination of the electronic cassette 32 and the radiation source 130 is stored in the HDD 110, but the invention is not limited thereto. For example, in a case where one radiation generating unit 34 and one electronic cassette 32 are used for the radiation information system 10, the correction information for correcting the radiographic image generated by the electronic cassette 321 is stored in the HDD 110. When the radiation source 130 installed in the radiation generating unit 34 is replaced, an alarm for urging updating of the correction information may be issued. In a case where a combination of the radiation generating unit 34 and the electronic cassette 32 is fixed, both thereof are not necessarily designated with the identification IDs.

In addition, in a case where one radiation generating unit 34 and a plurality of the electronic cassettes 32 is used for the radiation information system 10, the correction information for correcting the radiographic image generated by each electronic cassette 32 for every electronic cassette 32 is stored in the HDD 110. When the radiation source 130 installed in the radiation generating unit 34 is replaced, an alarm for urging updating of the correction information may be issued.

In addition, in the above exemplary embodiment, the electronic cassettes 32 and the radiation sources 130 are designated with identification IDs. However, alternatively, the one of each electronic cassette 32 and each radiation source 130 is designated with identification ID, and the other thereof stores identification ID which is used for the only combination thereof. The identification ID is acquired from the one of the electronic cassette 32 and the radiation source 130. If the acquired identification ID is not stored in the other of the electronic cassette 32 and the radiation source 130, an alarm may be issued.

Figure 7:
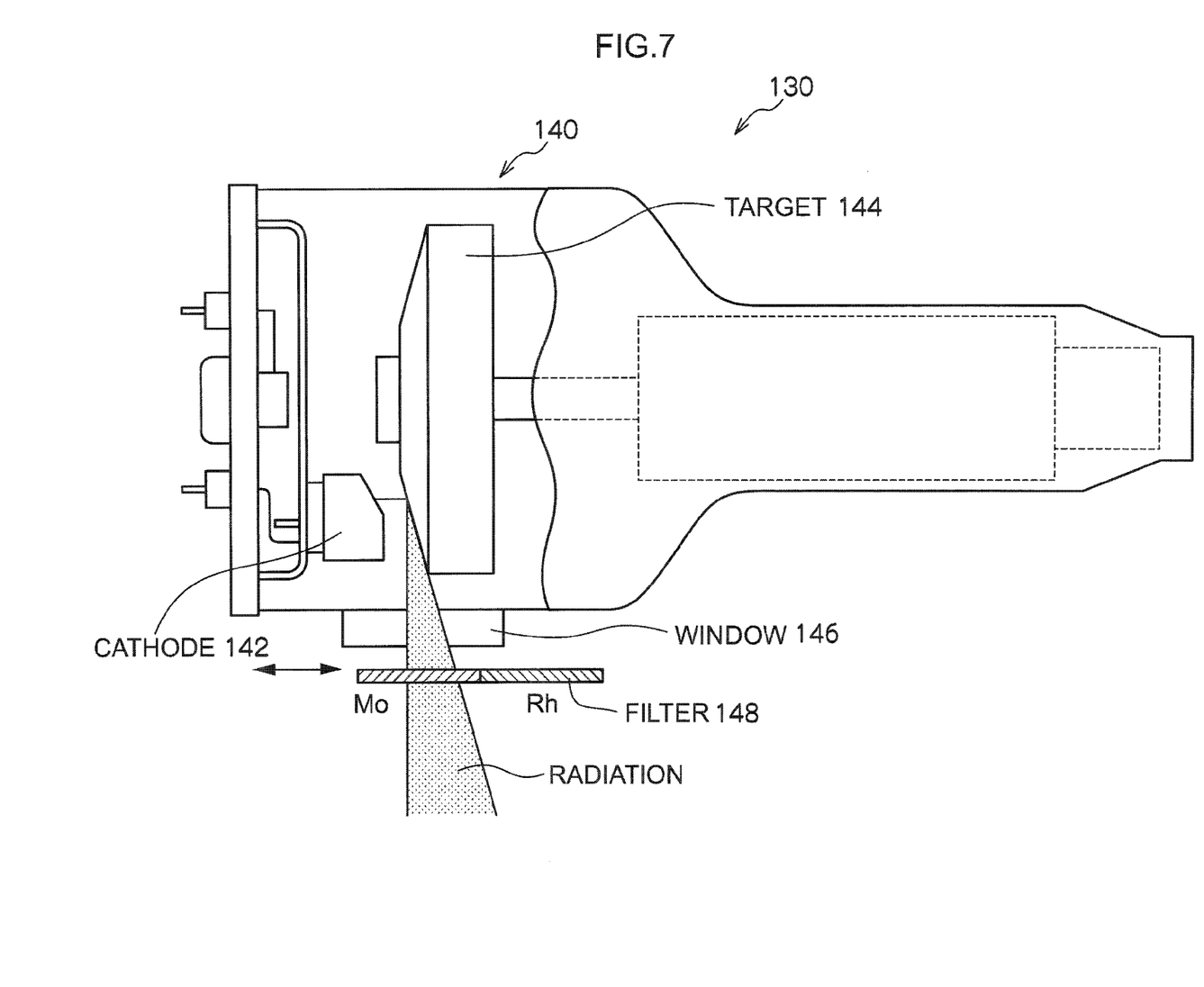
FIG. 7 is a cross-sectional view illustrating a structure of a radiation source according to an exemplary embodiment.

In addition, in the above exemplary embodiment, when the radiation source 130 is replaced, an alarm is issued, but the invention is not limited thereto. For example, as shown in FIG. 7, the radiation source 130 includes a cathode 142 having a filament and a target (anode) 144 made of molybdenum (Mo) in a casing 140. Thermal electrons emitted from the cathode 144 are accelerated and focused by a potential difference between the cathode and the anode to collide against the target 144, so that the X-ray is generated. The generated X-ray is irradiated out from a beryllium window 146 provided to the casing 140. In the radiation source 130 shown in FIG. 7, a membrane of molybdenum or rhodium (Rh) as a filter is disposed over the window 146. In the radiation source 130, the cathode 142, the target 144, or the filter 148 other than the entire radiation source 130 may be replaced. If the cathode 142, the target 144, or the filter 148 is replaced, the characteristics of the radiation irradiated from the radiation source 130 may be varied. Therefore, in a case where the cathode 142, the target 144, or the filter 148 is replaced, an alarm may be issued.

Further, the radiation source 130 may be provided with a collimator (not shown) which limits radiation region, and an alarm may be issued when the collimator is replaced.

In addition, in the above exemplary embodiment, the alarm is displayed on the display 100, so that the alarm can be issued to the doctor or the radiographic technologist, but the invention is not limited thereto. For example, an alarm sound may be output by using a sound reproducing apparatus such as a speaker, or an alarm text may be output. In addition, a combination of the alarm displaying on the display 100, the alarm sound output from the speaker, and the alarm text output may be used.

In addition, in the above exemplary embodiment, the console 42 receives the identification ID stored in the storage unit 130A of the radiation source 130 through the communication cable 35, and the console 42 receives the identification ID of the electronic cassette 32 stored in the storage unit 92C through wireless communication, but the invention is not limited thereto. For example, the identification ID may be acquired by reading out code information that is formed by coding the identification ID attached on a surface of the radiation source 130 or the electronic cassette 32. Alternately, the identification ID may be acquired by inputting the identification ID.

In the above exemplary embodiment, the construction (refer to FIG. 1) of the radiation information system 10, the construction (refer to FIGS. 2 and 4) of the imaging system 18, and the construction (refer to FIG. 3) of the electronic cassette 32 are exemplary ones. Therefore, these constructions may be modified without departing from the sprit and scope of the invention.

In addition, in the above exemplary embodiment, the procedure (refer to FIG. 6) of the combination determining process program is also an exemplary one. Therefore, these constructions may be modified without departing from the sprit and scope of the invention.

What is claimed is:

1. An image capturing control apparatus comprising:
a communication unit which communicates with a radiographic imaging apparatus which captures a radiographic image represented by irradiated radiation and generates image information indicating the captured radiographic image;
a radiation irradiating unit which is provided with a radiation source for generating the radiation and which irradiates the radiation from the radiation source;
a storage unit which stores correction information for correcting the radiographic image generated by the radiographic imaging apparatus; and
a controller which controls an alarm unit to issue an alarm in a case where the radiation source provided to the radiation irradiating unit, or a part which influences irradiation by the radiation source, is replaced due to being worn-out or in disorder.

2. The image capturing control apparatus of claim 1, wherein each radiographic imaging apparatus is designated by identification information, and
wherein the storage unit stores the correction information for correcting the radiographic image generated by a respective radiographic imaging apparatus for each radiographic imaging apparatus.

3. The image capturing control apparatus of claim 1, wherein each radiographic imaging apparatus and radiation source is respectively designated by identification information,
wherein the storage unit stores the correction information for correcting a radiographic image for each combination of a radiographic imaging apparatus and a radiation source,
wherein the image capturing control apparatus further comprises an acquisition unit which acquires the identification information of a radiographic imaging apparatus which can communicate with the communication unit and identification information of the radiation source which is provided to the radiation irradiating unit, and
wherein the controller controls the alarm unit to issue an alarm in a case where the correction information corresponding to the combination of the radiographic imaging apparatus and the radiation source, which is indicated by the identification information of the radiographic imaging apparatus and the radiation source acquired by the acquisition unit, is not stored in the storage unit.

4. The image capturing control apparatus of claim 1, wherein at least one of the radiographic imaging apparatus or the radiation source is designated by identification information, and the other of the radiographic imaging apparatus or the radiation source stores identification information of the one of the radiographic imaging apparatus or the radiation source that has been used in combination therewith,
wherein the image capturing control apparatus further comprises an acquisition unit which acquires the identification information from the one of the radiographic imaging apparatus or the radiation source, and
wherein the controller controls the alarm unit to issue an alarm in a case where the identification information acquired by the acquisition unit is not stored in the other of the radiographic imaging apparatus or the radiation source.

5. The image capturing control apparatus of claim 1, wherein the controller controls the radiation irradiating unit and the radiographic imaging apparatus to generate the correction information after the alarm unit issues an alarm.

6. The image capturing control apparatus of claim 1, wherein the part is one of a cathode, an anode, or a filter.

* * * * *